(12) United States Patent
Penhale et al.

(10) Patent No.: US 9,533,060 B2
(45) Date of Patent: Jan. 3, 2017

(54) RADIATION SOURCE ASSEMBLY

(75) Inventors: Douglas Penhale, London (CA); Joseph Elku, Tillsonburg (CA)

(73) Assignee: Trojan Technologies Inc., London (CA)

( * ) Notice: Subject to any disclaimer, the term of this patent is extended or adjusted under 35 U.S.C. 154(b) by 248 days.

(21) Appl. No.: 13/380,676

(22) PCT Filed: Jun. 30, 2010

(86) PCT No.: PCT/CA2010/001003
§ 371 (c)(1),
(2), (4) Date: Feb. 27, 2012

(87) PCT Pub. No.: WO2011/000091
PCT Pub. Date: Jan. 6, 2011

(65) Prior Publication Data
US 2012/0153183 A1    Jun. 21, 2012

Related U.S. Application Data

(60) Provisional application No. 61/213,685, filed on Jul. 2, 2009.

(51) Int. Cl.
*A61L 2/10* (2006.01)
*C02F 1/32* (2006.01)
(Continued)

(52) U.S. Cl.
CPC ............... *A61L 2/10* (2013.01); *C02F 1/325* (2013.01); *H01J 9/003* (2013.01); *H01J 61/28* (2013.01);
(Continued)

(58) Field of Classification Search
CPC ......... A61L 2/10; A61L 2202/11; H01J 9/003; H01J 61/28; H01J 61/523; C02F 1/325; C02F 2201/004; C02F 2201/3225; C02F 2201/3227
(Continued)

(56) References Cited

U.S. PATENT DOCUMENTS 2,004,564 A    6/1935   Bol
5,019,256 A    5/1991   Ifill et al.
(Continued)

FOREIGN PATENT DOCUMENTS

CN    101415486    1/2006

OTHER PUBLICATIONS

Communication: Publication of International Search Report for International Patent Application No. PCT/CA2010/001003 mailed Oct. 6, 2010.
Office Action for Canadian Application No. 2,764,918 with a mailing date of Jul. 6, 2015.
Second Office Action for Chinese Application No. 201080029551.0 with a mailing date of Nov. 15, 2014.
(Continued)

*Primary Examiner* — Michael Maskell
(74) *Attorney, Agent, or Firm* — Katten Muchin Rosenman LLP

(57) ABSTRACT

There is described In another of its aspects, the present invention provides a radiation source assembly comprising: (i) an elongate radiation source; (ii) a positioning element connected to a proximal portion of the elongate radiation source; and (iii) a connecting portion secured to a proximal portion of the positioning element and configured to engage a support element to maintain a distal portion of the elongate radiation source in a cantilevered position. The present radiation source assembly is configured such that the distal portion of the radiation source is cantilevered with the respect to the distal portion of the protective sleeve in which it is disposed. This feature obviates the need to use spacers, stops, springs and the like in a distal portion of the protective
(Continued)

sleeve to maintain correct position of the radiation source within the protective sleeve. Further, the present radiation source assembly is advantageous in that allows for withdrawal of the radiation source from the radiation source assembly without the need to disengage all of the components. Thus, it is possible to replace a single radiation source by removing it from the protective sleeve during operation of the fluid treatment system. This operation can be accomplished quickly without the need to shut down the fluid treatment system or otherwise compensate for the fact that one of the radiation source is being serviced.

25 Claims, 15 Drawing Sheets

(51) Int. Cl.
    *H01J 61/28*     (2006.01)
    *H01J 61/52*     (2006.01)
    *H01J 9/00*     (2006.01)

(52) U.S. Cl.
    CPC .......... *H01J 61/523* (2013.01); *A61L 2202/11* (2013.01); *C02F 2201/004* (2013.01); *C02F 2201/3225* (2013.01); *C02F 2201/3227* (2013.01)

(58) Field of Classification Search
    USPC ................. 250/428, 429, 432 R, 435, 436
    See application file for complete search history.

(56) References Cited

U.S. PATENT DOCUMENTS

| | | | |
|---|---|---|---|
| 5,418,370 A * | 5/1995 | Maarschalkerweerd | ............................ B01J 19/123 250/431 |
| 6,674,084 B2 * | 1/2004 | Sarchese | ................... A61L 2/10 250/436 |
| 6,984,834 B2 | 1/2006 | Alexander et al. | |
| 7,390,406 B2 * | 6/2008 | Traubenberg | ........... C02F 1/325 210/198.1 |
| 7,408,174 B2 * | 8/2008 | From | ....................... A61L 2/10 250/428 |
| 2002/0190220 A1 | 12/2002 | Sarchese et al. | |
| 2007/0284540 A1 * | 12/2007 | Matthews | ............... C02F 1/325 250/436 |
| 2009/0065413 A1 * | 3/2009 | Fraser | .................... H01J 61/52 210/175 |

OTHER PUBLICATIONS

Third Office Action for Chinese Application No. 201080029551.0 with a mailing date of May 21, 2015.
Extended European search report for European Patent Application No. 10 79 3468 with a mailing date of Dec. 5, 2014.
International Search Report dated Sep. 29, 2010.
Canadian Office Action dated May 7, 2013 for Canadian Appln. No. 2,764,918.
Chinese Office Action dated Jan. 17, 2014 for Chinese Appln. No. 201080029551.0.
Fourth Chinese Office Action dated Feb. 3, 2016.

* cited by examiner

RADIATION SOURCE ASSEMBLY

CROSS-REFERENCE TO RELATED APPLICATION

This application is a national stage of PCT/CA2010/001003, filed on Jun. 30, 2010, which claims priority to U.S. Provisional Patent Application No. 61/213,685, filed on Jul. 2, 2009. Each of these documents is incorporated herein by reference in its entirety.

BACKGROUND OF THE INVENTION

Field of the Invention

In one of its aspects, the present invention relates to a radiation source assembly. In another of its aspects, the present invention relates to a radiation source module comprising a plurality of radiation source assemblies. Other aspects of the invention will become apparent to those of skill in the art upon reviewing the present specification.

Description of the Prior Art

Fluid treatment systems are known generally in the art. For example, U.S. Pat. Nos. 4,482,809, 4,872,980 and 5,006,244 [all in the name of Maarschalkerweerd and hereinafter referred to as the Maarschalkerweerd Patents] all describe gravity fed fluid treatment systems which employ ultraviolet (UV) radiation.

Such systems include an array of UV lamp frames which include several UV lamps each of which are mounted within sleeves which extend between and are supported by a pair of legs which are attached to a cross-piece. The so-supported sleeves (containing the UV lamps) are immersed into a fluid to be treated which is then irradiated as required. The amount of radiation to which the fluid is exposed is determined by the proximity of the fluid to the lamps, the output wattage of the lamps and the fluid's flow rate past the lamps. Typically, one or more UV sensors may be employed to monitor the UV output of the lamps and the fluid level is typically controlled, to some extent, downstream of the treatment device by means of level gates or the like.

In recent years, there has been interest in the so-called "transverse-to-flow" fluid treatment systems. In these systems, the radiation source is disposed in the fluid to be treated in a manner such that the longitudinal axis of the radiation source is in a transverse (e.g., substantially orthogonal or vertical orientation of the radiation sources) relationship with respect to the direction of fluid flow past the radiation source. See, for example, any one of:

International Publication Number WO 2004/000735 [Traubenberg et al.];

International Publication Number WO 2008/055344 [Ma et al.];

International Publication Number WO 2008/019490 [Traubenberg et al.];

U.S. Pat. No. 7,408,174 [From et al.];

U.S. provisional patent application Ser. No. 61/193,686 [Penhale et al.], filed Dec. 16, 2008; and U.S. provisional patent application Ser. No. 61/202,576 [Penhale et al.], filed Mar. 13, 2009.

Conventionally, when radiation source assemblies were used in a vertical configuration in a fluid treatment system, it has been known to use springs, stoppers, spacers and other support elements to receive the bottom portion of the radiation source in the assemblies for the purpose of supporting the radiation source and positioning it properly within the protective sleeve. The conventional radiation sources would have electrical pins that would be received by a module plug which would then be connected to an electrical supply (e.g., a ballast or similar power supply)—see, for example, the Maarschalkerweerd Patents referred to above.

When it becomes necessary to service the lamp (e.g., to replace it after its service life has been or is about to be exceeded), it is commonly necessary to remove the radiation source assembly from the fluid treatment system and effectively disassemble it to access the various components. This is cumbersome and increases maintenance costs for the fluid treatment system. This is especially so given that many of these radiation sources are three feet (or longer) in length and significant care must be exercised to avoid breakage of one or both of the radiation source and the protective sleeve in which it is disposed.

In addition, conventional radiation sources used in the fluid treatment systems typically contain a metal-containing amalgam composition. The temperature of this metal-containing amalgam composition is important to maintain optimal operation of the radiation source. The prior art has not specifically addressed the issue of appropriate temperature control for metal-containing amalgam compositions for radiation sources that are disposed in a vertical orientation in a fluid treatment system.

Accordingly, it would be desirable to have a radiation source assembly that obviates or mitigates at least one of the above-mentioned problems of the prior art.

SUMMARY OF THE INVENTION

It is an object of the present invention to obviate or mitigate at least one of the above-mentioned disadvantages of the prior art.

It is another object of the present invention to provide a novel radiation source assembly.

It is another object of the present invention to provide a novel radiation source module.

It is another object of the present invention to provide a novel fluid treatment system.

Accordingly, in one of its aspects, the present invention provides a radiation source assembly comprising:

(i) an elongate radiation transparent protective sleeve;

(ii) an elongate radiation source disposed in the protective sleeve;

(iii) a positioning element connected to a proximal portion of the elongate radiation source;

(iv) a connecting portion secured to a proximal portion of the positioning element; and (v) a support element configured to receive the connecting portion to maintain a distal portion of the elongate radiation source in a cantilevered position with respect to a distal portion of the protective sleeve.

The invention also relates to a radiation source module and to a fluid treatment system incorporating this radiation source assembly.

In another of its aspects, the present invention provides a radiation source assembly comprising:

(i) an elongate radiation source;

(ii) a positioning element connected to a proximal portion of the elongate radiation source; and (iii) a connecting portion secured to a proximal portion of the positioning element and configured to engage a support element to maintain a distal portion of the elongate radiation source in a cantilevered position.

Thus, the present inventors have developed a novel radiation source assembly which obviate or mitigates one or more of the above-mentioned problems of the prior art. Specifically, the present radiation source assembly is configured such that the distal portion of the radiation source is cantilevered with the respect to the distal portion of the protective sleeve in which it is disposed. This feature obviates the need to use spacers, stops, springs and the like in a distal portion of the protective sleeve to maintain correct position of the radiation source within the protective sleeve. Further, the present radiation source assembly is advantageous in that it allows for withdrawal of the radiation source from the radiation source assembly without the need to disengage all of the components. Thus, it is possible to replace a single radiation source by removing it from the protective sleeve during operation of the fluid treatment system. This operation can be accomplished quickly without the need to shut down the fluid treatment system or otherwise compensate for the fact that one of the radiation sources is being serviced.

The provision of a positioning element movably connected to a proximal portion of the radiation source prevents the creation of a large moment being placed on the radiation source. This obviates or mitigates bending or cracking of the radiation source and/or the protective sleeve in which it is disposed.

Further, the present inventors have developed an approach to optimize the temperature of the metal containing amalgam composition by locating this composition and an appropriate control system at a distal portion of the radiation source.

Further, the present radiation source assembly obviates or mitigates the need to use relatively expensive modular plug elements connection the radiation source to the power supply.

Other advantages of the invention will become apparent to those of skill in the art upon reviewing the present specification.

BRIEF DESCRIPTION OF THE DRAWINGS

Embodiments of the present invention will be described with reference to the accompanying drawings, wherein like reference numerals denote like parts, and in which.

DETAILED DESCRIPTION OF THE PREFERRED EMBODIMENTS

Figure 1:
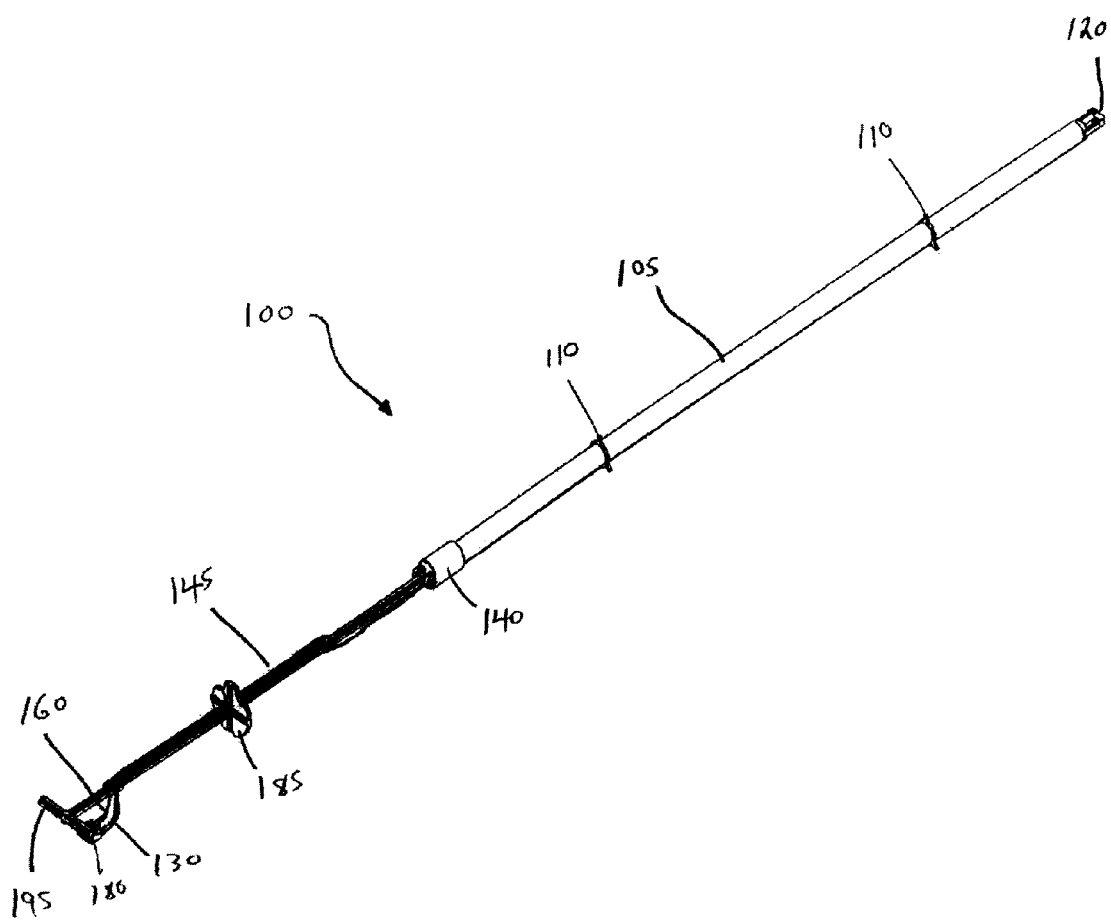
FIG. 1 illustrates a perspective view of a preferred embodiment of the present radiation source assembly.
Figure 2:
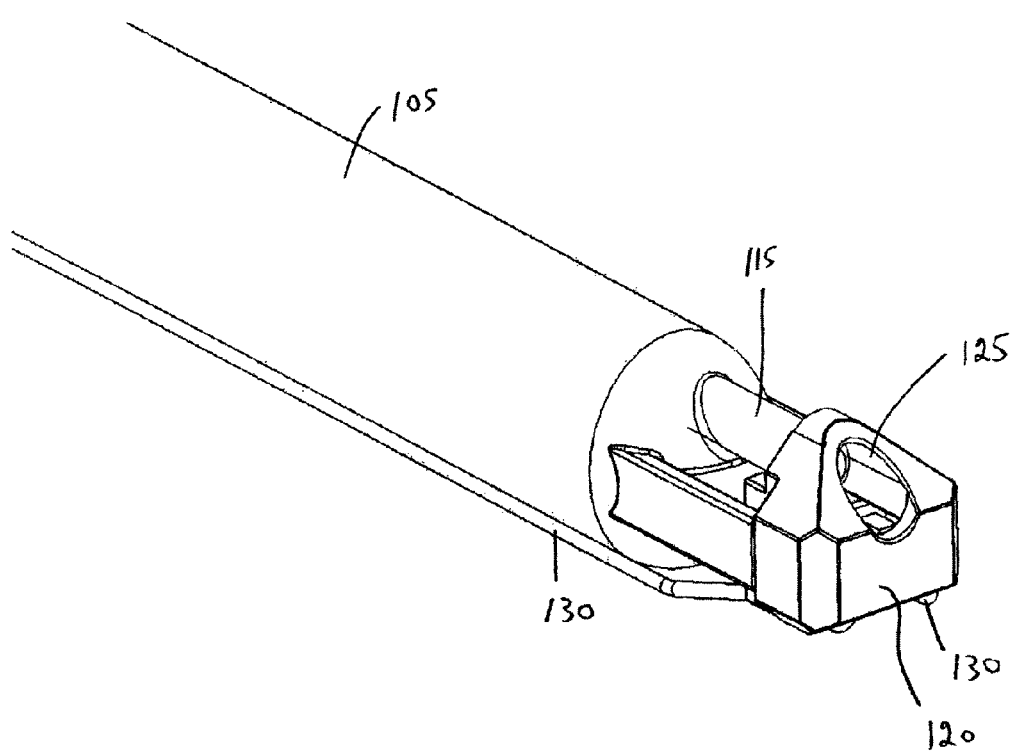
FIG. 2 illustrates an enlarged perspective view of the distal portion of the radiation source assembly illustrated in FIG. 1.
Figure 3:
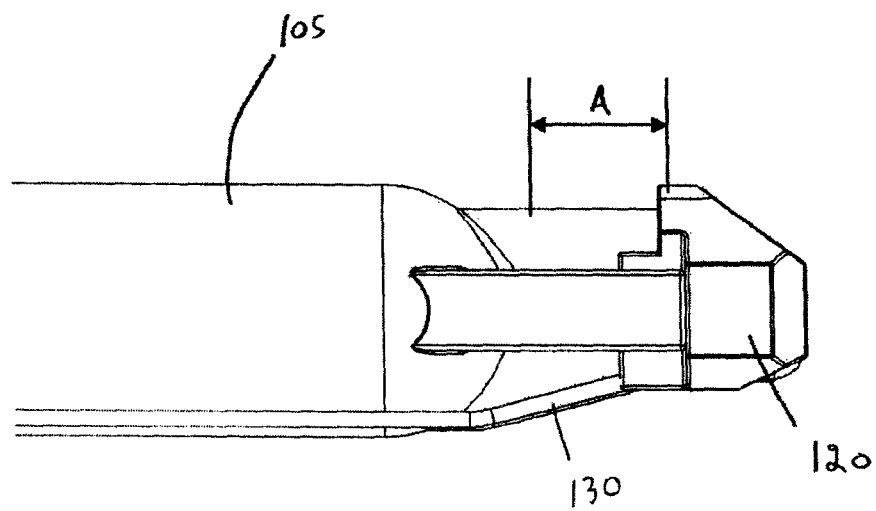
FIG. 3 illustrates an enlarged side elevation of a distal portion of the radiation source assembly illustrated in FIG. 1.
Figure 4:
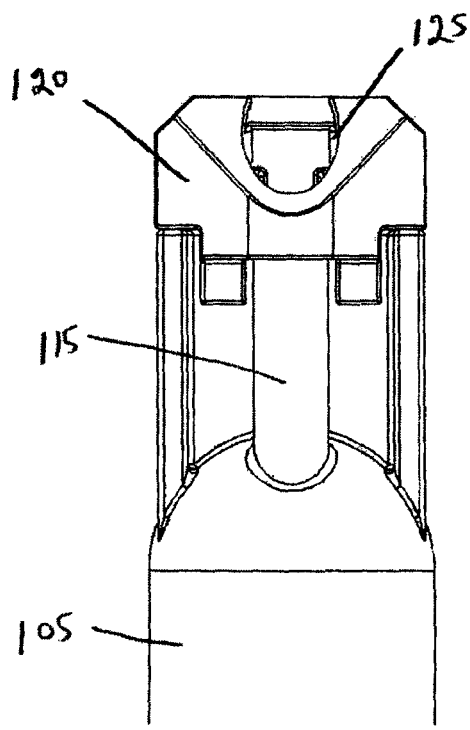
FIG. 4 illustrates an enlarged top view of a distal portion of the radiation source assembly illustrated in FIG. 1.
Figure 5:
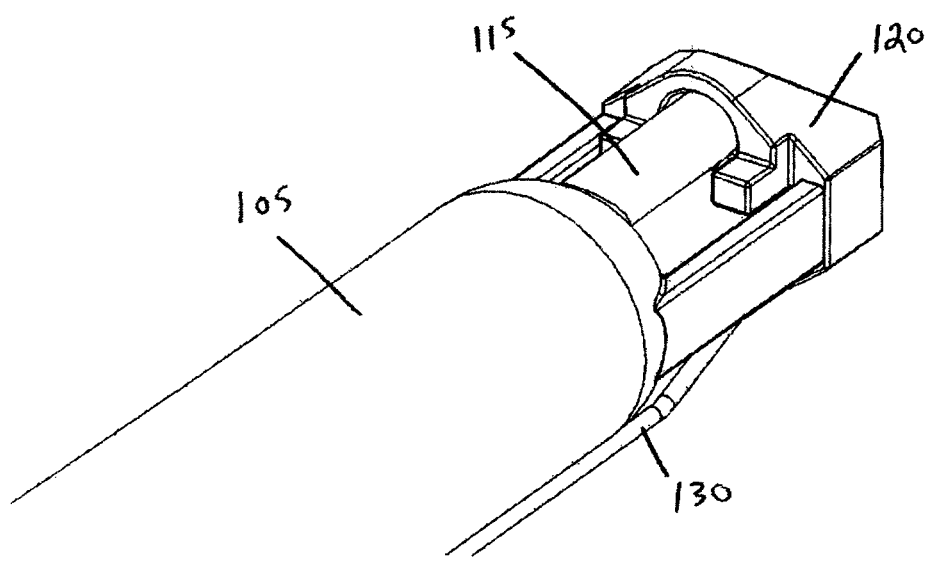
FIGS. 5 and 6 illustrate enlarged isometric views of a distal portion of the radiation source assembly illustrated in FIG. 1.
Figure 6:
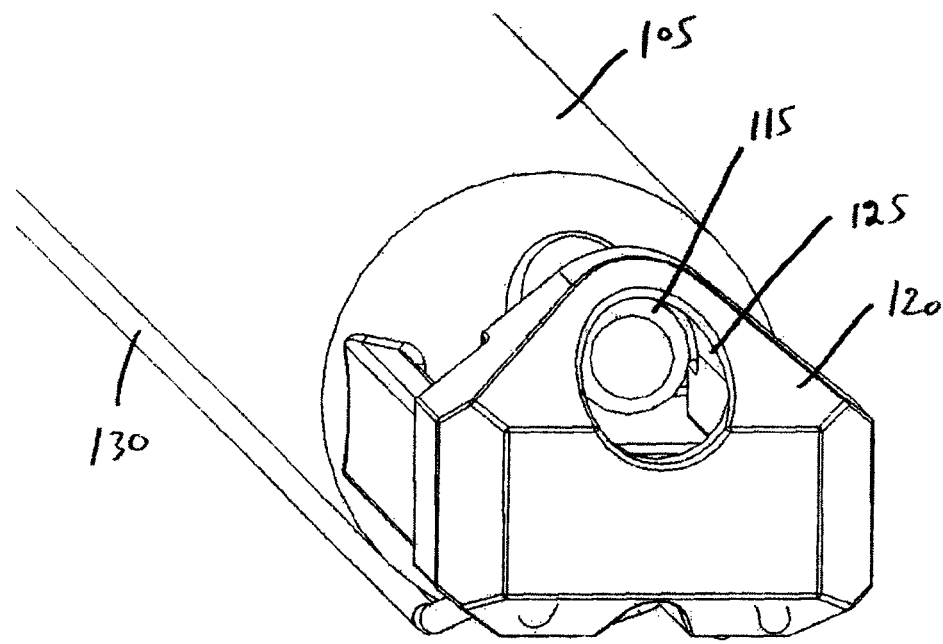

In one of its aspects, the present invention relates to a radiation source assembly comprising: (i) an elongate radiation transparent protective sleeve; (ii) an elongate radiation source disposed in the protective sleeve; (iii) a positioning element connected to a proximal portion of the elongate radiation source; (iv) a connecting portion secured to a proximal portion of the positioning element; and (v) a support element configured to receive the connecting portion to maintain a distal portion of the elongate radiation source in a cantilevered position with respect to a distal portion of the protective sleeve. Preferred embodiments of this radiation source assembly may include any one or a combination of any two or more of any of the following features:

- the connecting portion may be in a movable relationship with respect to the proximal portion of the elongate radiation source;
- the connecting portion may be in a pivoting relationship with respect to the proximal portion of the elongate radiation source;
- the connecting portion may be in a rotatable relationship with respect to the proximal portion of the elongate radiation source;
- the protective sleeve may comprise a proximal open end and a distal closed end;
- the protective sleeve may comprise a pair of open ends;
- a distal end of the protective sleeve may comprise a sealing element to substantially prevent ingress of fluid to the interior of the protective sleeve;
- the protective sleeve may be constructed of quartz;
- the elongate radiation source may comprise at least one centering ring to maintain the elongate radiation source and the elongate protective sleeve in a spaced (e.g., substantially coaxial) relationship with one another;
- the elongate radiation source may comprise a plurality of centering rings to maintain the elongate radiation source and the elongate protective sleeve in a spaced (e.g., substantially coaxial) relationship with one another;
- the positioning element may comprise at least one loom portion to secure an electrical connecter from the elongate radiation source along a portion of the length of the positioning element;
- the positioning element may comprise at least one loom portion to secure a plurality of electrical connecters from the elongate radiation source along a portion of the length of the positioning element;
- the positioning element may comprise a plurality of loom portions to secure an electrical connecter from the elongate radiation source along a portion of the length of the positioning element;
- the positioning element may comprise a plurality of loom portions to secure a plurality of electrical connecters from the elongate radiation source along a portion of the length of the positioning element;
- the elongate radiation source may comprise a reservoir portion containing a metal amalgam composition;

the reservoir portion may be disposed at the distal portion of the elongate radiation source;

the distal portion of the elongate radiation source may comprise an amalgam base portion secured thereto, the amalgam base portion receiving at least a portion of the reservoir portion;

the amalgam base portion may comprise at least one aperture configured to allow heat dissipation from the reservoir portion;

the amalgam base portion may further comprise a flap portion moveable between a first position in which the flap portion at least partially obstructs the aperture and a second position in which the aperture is unobstructed by the flap portion;

the amalgam base portion may further comprise a flap portion moveable between a first position in which the flap portion obstructs the aperture and a second position in which the aperture is unobstructed by the flap portion.

the flap portion may comprises a first metal and a second metal (different from the first metal);

the first metal and the second metal may thermally expand at different rates;

the metal amalgam composition may comprise a mercury amalgam composition.

the positioning element and the support element may be configured to have a single correct engagement position;

the elongate radiation source may be an ultraviolet radiation source;

the elongate radiation source may be a low pressure ultraviolet radiation source;

the elongate radiation source is a low pressure, high output ultraviolet radiation source;

the elongate radiation source is medium pressure ultraviolet radiation source;

Another aspect of the present invention relates to radiation source module comprising a support element for securing the module in a fluid treatment system and at least one radiation source assembly (preferably a plurality) as defined above.

Another aspect of the present invention relates to a fluid treatment system comprising a fluid treatment zone for receiving a flow of fluid and at least one radiation source module defined in the previous paragraph, wherein the at least one radiation source module is configured such that the radiation source assembly is disposed in the fluid treatment zone. Preferred embodiments of this fluid treatment system may include any one or a combination of any two or more of any of the following features:

the fluid treatment zone may be comprised in an open channel for receiving the flow of fluid;

the fluid treatment zone may be comprised in a closed channel for receiving the flow of fluid;

the at least one radiation source assembly may have a longitudinal axis disposed transverse to the direction of fluid flow through the fluid treatment zone;

the at least one radiation source assembly may have a longitudinal axis disposed orthogonal to the direction of fluid flow through the fluid treatment zone;

the at least one radiation source assembly may be disposed substantially vertically in the fluid treatment zone.

In one of its aspects, the present invention relates to a radiation source assembly comprising: (i) an elongate radiation source; (ii) a positioning element connected to a proximal portion of the elongate radiation source; and (iii) a connecting portion secured to a proximal portion of the positioning element and configured to engage a support element to maintain a distal portion of the elongate radiation source in a cantilevered position. Preferred embodiments of this radiation source assembly may include any one or a combination of any two or more of any of the following features:

the connecting portion may be in a movable relationship with respect to the proximal portion of the elongate radiation source;

the connecting portion may be in a pivoting relationship with respect to the proximal portion of the elongate radiation source;

the connecting portion may be in a rotatable relationship with respect to the proximal portion of the elongate radiation source;

the elongate radiation source may comprise at least one centering ring to maintain the elongate radiation source and the elongate protective sleeve in a spaced (e.g., substantially coaxial) relationship with one another;

the elongate radiation source may comprise a plurality of centering rings to maintain the elongate radiation source and the elongate protective sleeve in a spaced (e.g., substantially coaxial) relationship with one another;

the positioning element may comprise at least one loom portion to secure an electrical connecter from the elongate radiation source along a portion of the length of the positioning element;

the positioning element may comprise at least one loom portion to secure a plurality of electrical connecters from the elongate radiation source along a portion of the length of the positioning element;

the positioning element may comprise a plurality of loom portions to secure an electrical connecter from the elongate radiation source along a portion of the length of the positioning element;

the positioning element may comprise a plurality of loom portions to secure a plurality of electrical connecters from the elongate radiation source along a portion of the length of the positioning element;

the elongate radiation source may comprise a reservoir portion containing a metal amalgam composition;

the reservoir portion may be disposed at the distal portion of the elongate radiation source;

the distal portion of the elongate radiation source may comprise an amalgam base portion secured thereto, the amalgam base portion receiving at least a portion of the reservoir portion;

the amalgam base portion may comprise at least one aperture configured to allow heat dissipation from the reservoir portion;

the amalgam base portion may further comprise a flap portion moveable between a first position in which the flap portion at least partially obstructs the aperture and a second position in which the aperture is unobstructed by the flap portion;

the amalgam base portion may further comprise a flap portion moveable between a first position in which the flap portion obstructs the aperture and a second position in which the aperture is unobstructed by the flap portion;

the flap portion may comprise a first metal and a second metal;

the first metal and the second metal may thermally expand at different rates;

the metal amalgam composition may comprise a mercury amalgam composition;

the positioning element may be configured to have a single correct engagement position with the support element;

the elongate radiation source may be an ultraviolet radiation source;

the elongate radiation source may be a low pressure ultraviolet radiation source;

the elongate radiation source may be a low pressure, high output ultraviolet radiation source;

the elongate radiation source may be a medium pressure ultraviolet radiation source; and the angled base portion provides physical protection for the lamp and the reservoir portion.

With reference to FIGS. 1-9 and 14-16, there is illustrated a radiation source assembly 100. Radiation source assembly 100 comprises a radiation source 105 which may be an ultraviolet lamp or any other radiation emitting lamp. Disposed on radiation source 105 are a pair of centering rings 110. Centering rings 110 serve to position radiation source 105 spaced (e.g., substantially coaxially) with respect to a protective sleeve (not shown for clarity). Centering rings 110 may be made from a radiation resistant material such as Teflon™.

Disposed at the distal portion of radiation source 105 is an amalgam reservoir 115 which contains a metal-containing amalgam composition (e.g., a mercury-containing amalgam composition). Also disposed in the distal portion of radiation source 105 is an amalgam end base 120.

Amalgam end base 120 is configured to have an aperture 125 which receives a portion of amalgam reservoir 115. As shown particularly in FIG. 3, Dimension A generally represents the exposed region of amalgam reservoir 115 with respect to amalgam end base 120. Dimension A may be varied appropriately to expose sufficient portion of amalgam reservoir 115 to the surrounding environment optimizing heat dissipation from amalgam reservoir 115 and proper operation of radiation source 105. Emanating from amalgam end base 120 are a pair of electrical leads 130.

Figure 7:
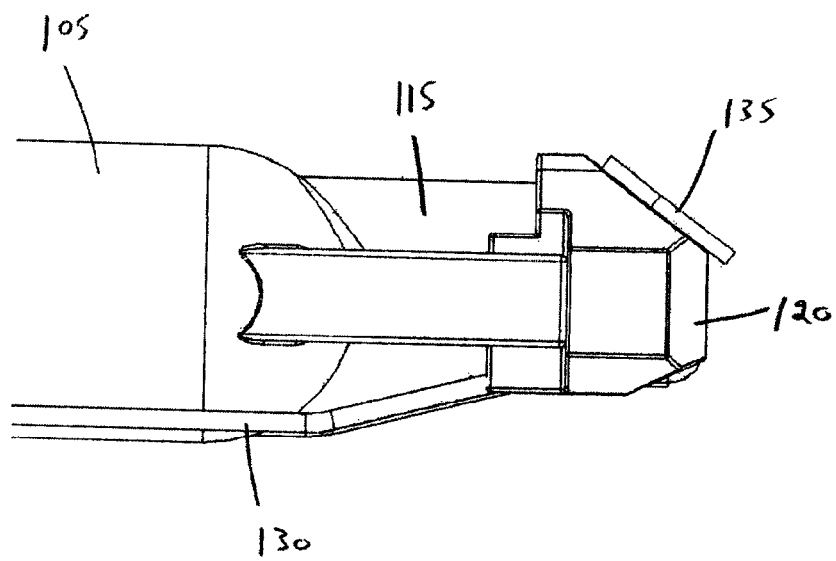
FIG. 7 illustrates a side elevation of a modified form of a distal portion of the radiation source assembly illustrated in FIG. 1.
Figure 8:
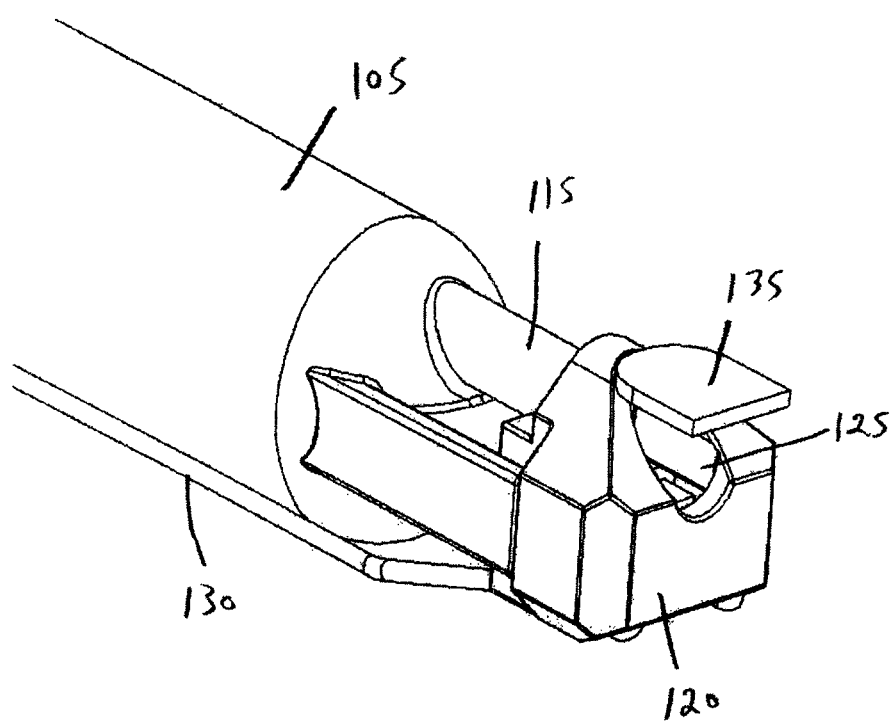
FIG. 8 illustrates an isometric view of the modified form of the distal portion of the radiation source assembly illustrated in FIG. 7.

With reference to FIGS. 7 and 8, a modified version of amalgam end base 120 is illustrated. In this modification, a flap portion 135 is pivotally attached to amalgam end base 120. Flap portion 135 is movable between a closed position (FIG. 7) and an open position (FIG. 8). In a preferred embodiment, flap portion 135 has a bi-metal construction. In this embodiment, flap portion 135 would consist of two different metals, preferably in a laminate construction. Each of the two metals would have a different thermal expansion property allowing flap portion 135 to open or close depending on the temperature of the surrounding environment. Thus, when it would be desirable to allow heat to dissipate from amalgam end base 120, flap portion 135 would open allowing heat to exit from aperture 125. Once the appropriate temperature of amalgam reservoir 115 is reached, flap portion 135 would then move to the closed position (FIG. 7).

Figure 9:
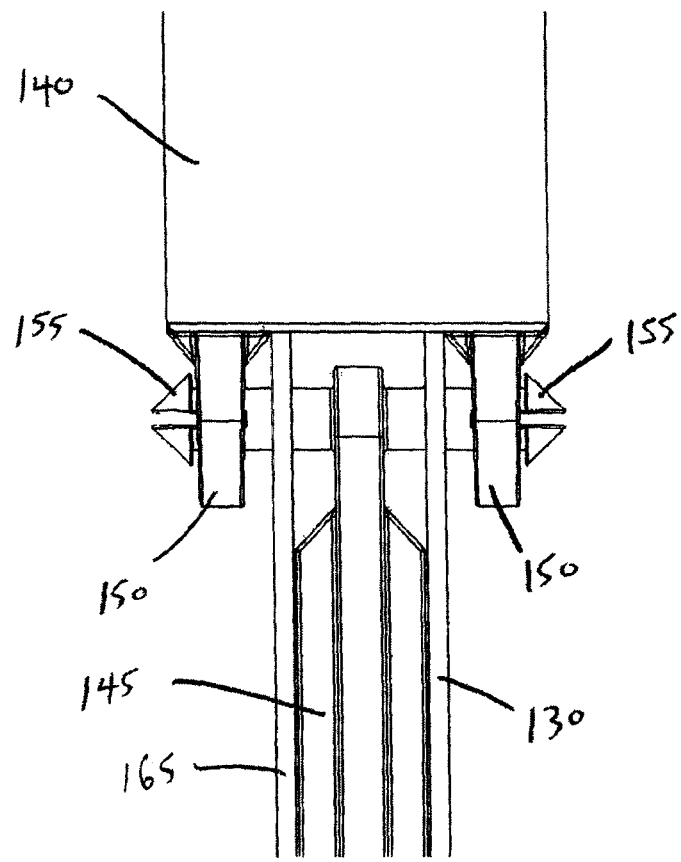
FIGS. 9-13 illustrate various embodiments of connecting the position element to a proximal portion of the radiation source.
Figure 10:
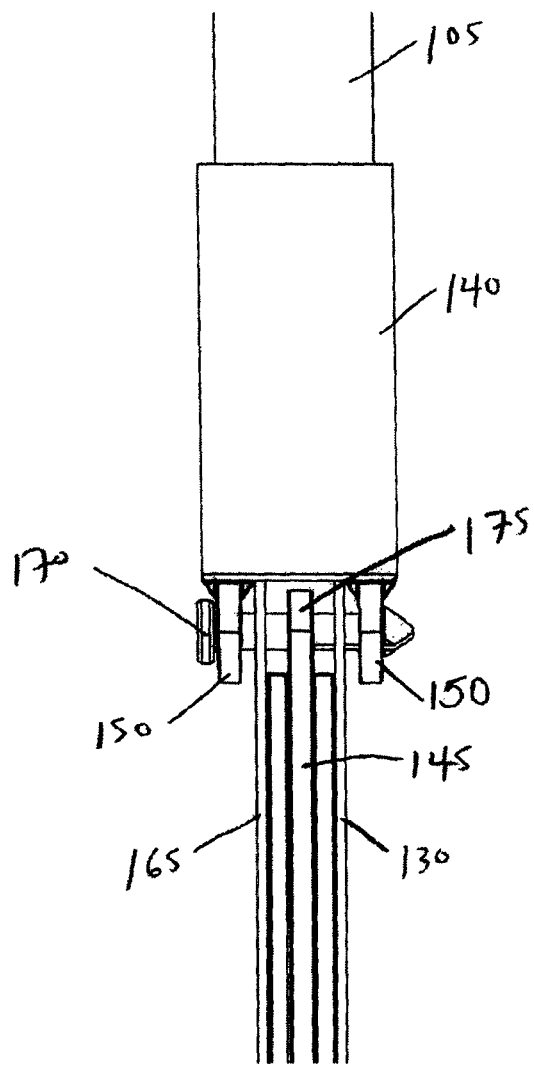
Figure 11:
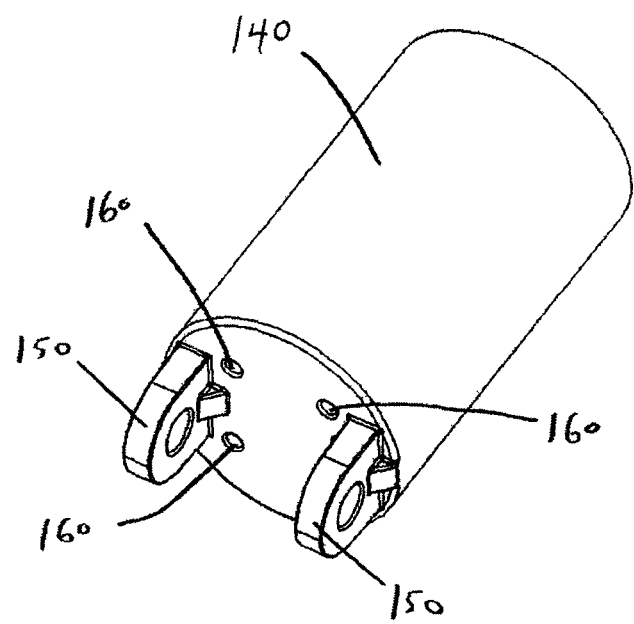

With reference to FIGS. 1, 9 and 10, it will be seen that the proximal portion of radiation source 105 has a fixed thereto an end base element 140. A positioning rod 145 is connected to a pair of ears 150 on end base element 140 by a pair of pin elements 155 that are integrally formed with positioning rod 145. With particular reference to FIG. 11, it will be seen that end base element 140 comprises a series of apertures 160 through with electrical leads (not shown for clarity) from radiation source 105 may emanate. Typically, there will be one or two electrical leads 130 emanating from a distal portion or radiation source 105 and one or two electrical leads 165 emanating from a proximal portion of radiation source 105. The number of electrical leads is not particularly restricted and will be depend on the nature of radiation source 105.

As will be understood, the connection of positioning rod 145 to end base element 140 allows for pivoting of these two elements with respect to one another. This facilitates placement and removal of radiation source assembly 100 in a protective sleeve thereby reducing the risk of increasing a bending moment on radiation source 105 and/or the protective sleeve minimizing the risk that either of these elements will be broken during servicing of radiation source 105.

With reference to FIG. 10, there is illustrated a small modification of the embodiment illustrated in FIG. 9. Specifically, in FIG. 10, the connection of positioning rod 145 to end base element 140 is accomplished by use of a pivot pin 170 which is independent of positioning rod 145. Specifically, pivot pin 170 traverses through ears 150 and an aperture (not shown) in distal portion 175 of positioning rod 145.

Figure 12:
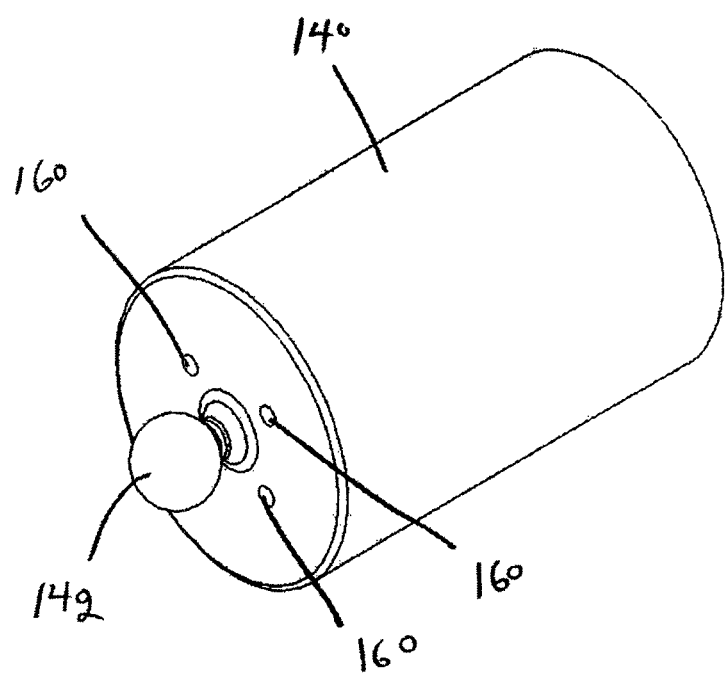
Figure 13:
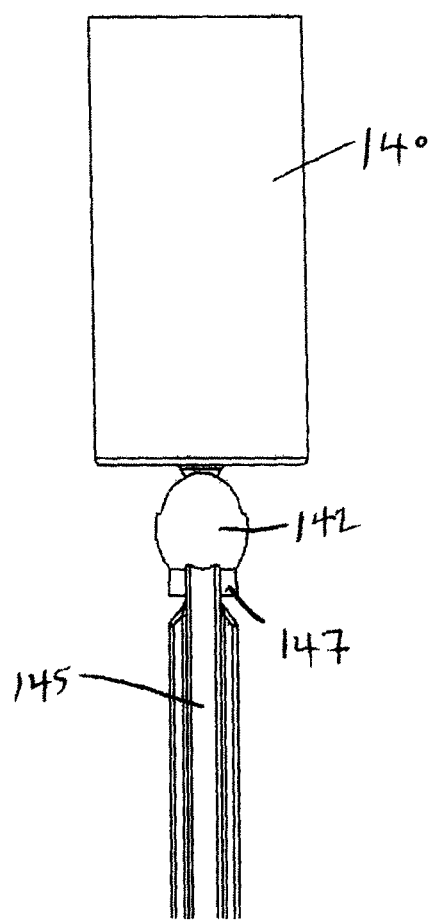

With reference to FIGS. 12 and 13, there is illustrated a modified form of end base element 140 which utilizes a so-called ball joint connected to positioning rod 145. Thus, end base element 140 comprises a ball portion 142 which is received in a complementary shaped base 147 on positioning rod 145.

Figure 14:
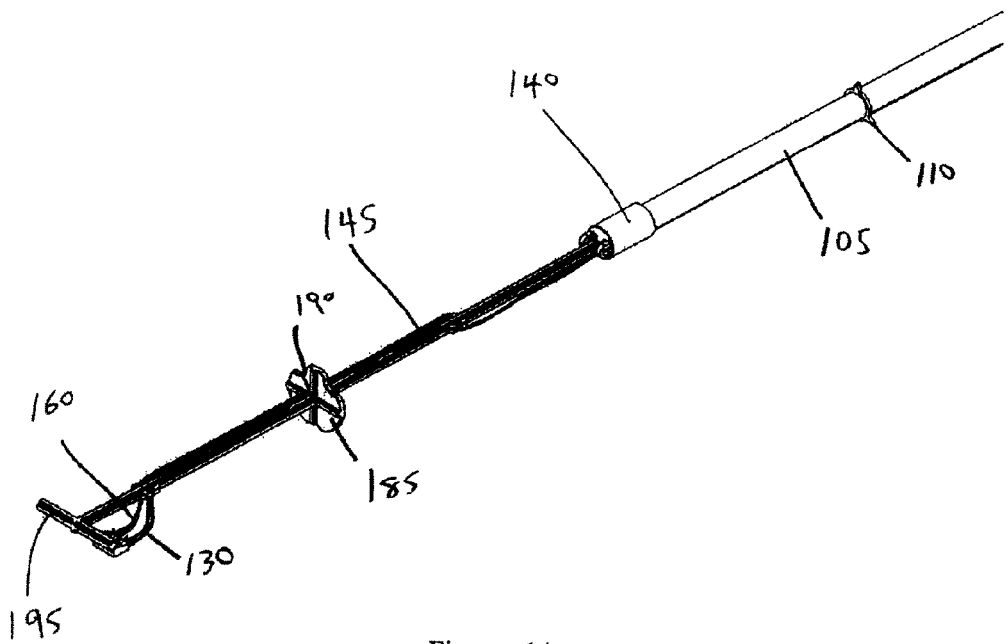
FIG. 14 illustrates a proximal portion of the radiation source assembly illustrated in FIG. 1.
Figure 15:
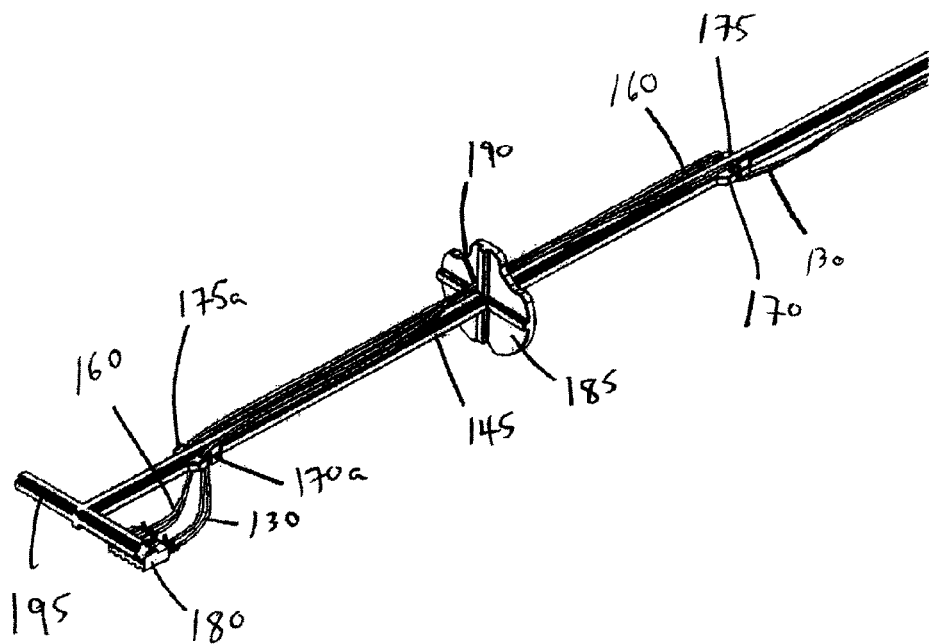
FIG. 15 illustrates an enlarged view of the embodiment shown in FIG. 14.
Figure 16:
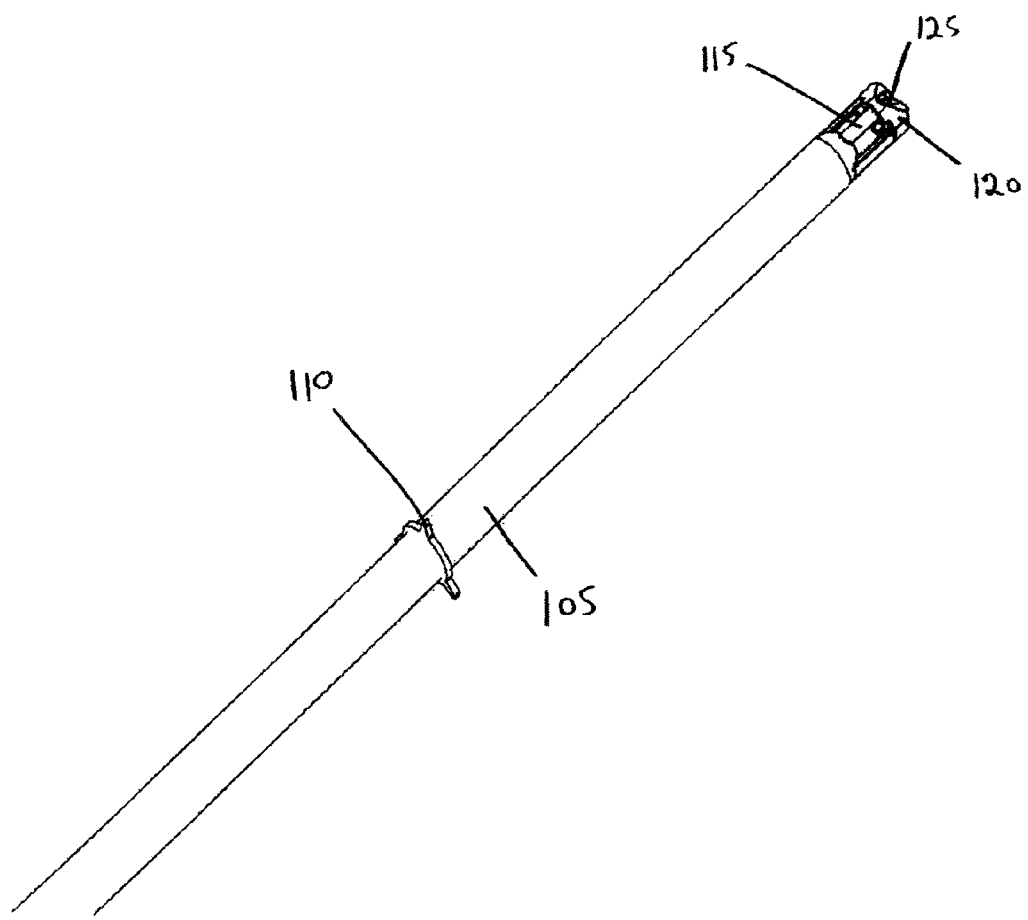
FIG. 16 illustrates a perspective view of a portion of the radiation source assembly illustrated in FIG. 1.

With reference to FIGS. 14 and 15, it can be seen that positioning rod 145 comprises a pair of looms 170,175. As illustrated, electrical leads 130 are fed through loom 170 while electrical leads 160 are fed through loom 175. Looms 170,175 may be configured and oriented with respect to one another, for example to keep the electrical leads out of the field of view of optical radiation sensor (not shown) if present in the system.

A second pair of looms 170a,175a are provided near the proximal portion of positioning rod 145 to receive electrical leads 130 and 160, respectively. As shown, electrical leads 130 and 160 are received in an electrical connector 180 which is conventional. The use of a conventional connector 180 allows for illumination of the need to use expensive molded-type connectors, for example, as shown in the Maarschalkerweerd Patents discussed above.

Positioning rod 145 further comprises a radiation block 185 which has a slot 190 for receiving electrical leads 130 and 160. Radiation block 185 serves to block radiation emanating upward and posing a potential occupation health risk to operators of the fluid treatment system.

The proximal portion of positioning rod 145 comprises a handle 195 in the form of a cross piece connection to positioning rod 145.

Figure 17:
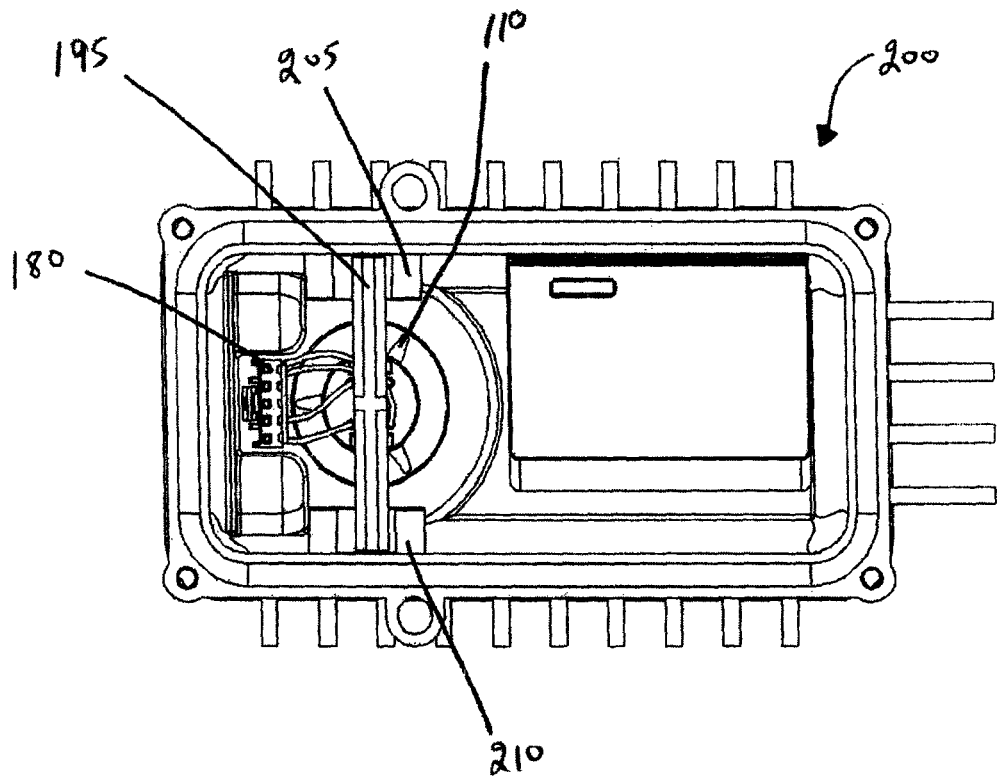
FIGS. 17 and 18 illustrate positioning of the radiation source assembly in a support member.
Figure 18:
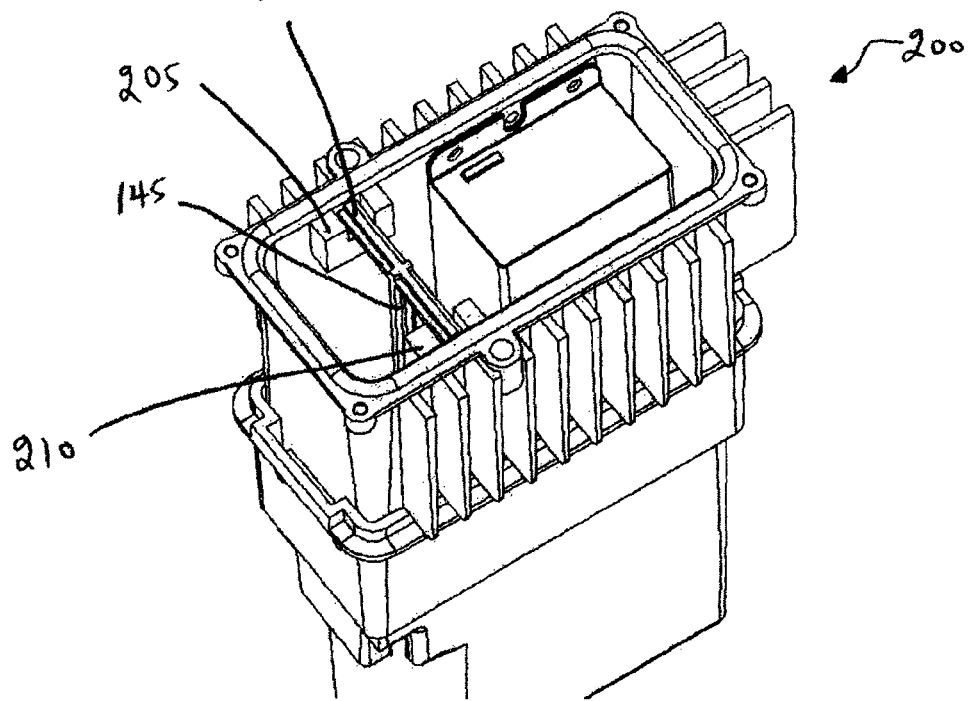

With reference to FIGS. 17 and 18, there is illustrated a cartridge element 200 which is of similar construction to the radiation source cartridge described in illustrated in U.S. provisional patent application Ser. No. 61/193,686 [Penhale et al.] filed Dec. 16, 2008.

Cartridge element 200 illustrated in FIGS. 17 and 18 includes a pair of support elements 205,210 which receive handle 195 of positioning rod 145. Preferably, handle 195 and support elements 205,210 are indexed or keyed so that handle 195 is engaged with support elements 205,210 in a singular correct position. This facilitates ensuring that electrical leads 130 and 160 do not obscure any optical radiation sensors that may be used in the fluid treatment system.

With further reference to FIG. 17, it can be seen that electrical connector 180 is connected to a complementary connector on cartridge element 200 (the electrical connections are omitted from FIG. 18 for clarity).

The connection of the protective sleeve (not shown) in which radiation source 105 is disposed to cartridge element 200 is conventional—see, for example, the teachings of U.S. provisional patent application Ser. No. 61/193,686 [Penhale et al.], filed Dec. 16, 2008.

When it is desired to service radiation source 105, electrical connector 180 is disengaged and handle 195 is lifted from support elements 205,210 thereby lifting radiation source 105 out of the protective sleeve (not shown). As end base element 140 emanates from cartridge element 200, the pivoting movement of positioning rod 145 with respect to radiation source 105 allows simpler withdrawal of radiation source 105 from the protective sleeve. This avoids conferring a bending moment to radiation source 105 and/or the protective sleeve (not shown), thereby obviating or mitigating breakage of these components. Of particular note, the protective sleeve may be left in place while radiation source 105 is being serviced.

Figure 19:
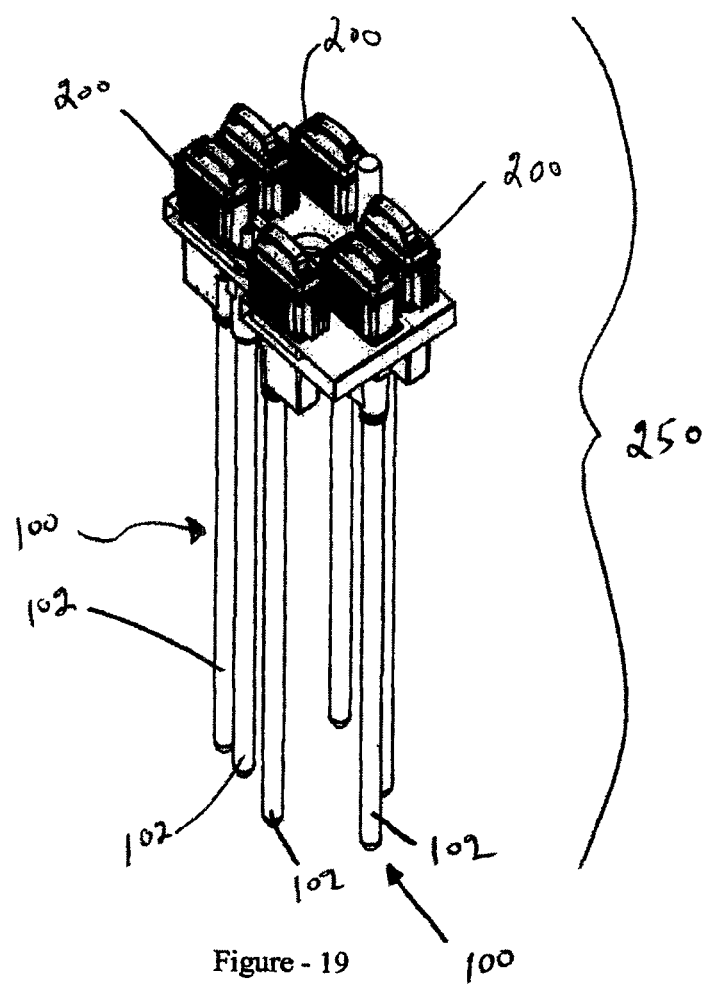
FIG. 19 illustrates a perspective view of a radiation source module containing a number of radiation source assemblies illustrated in FIG. 1.

With reference to FIG. 19, there is illustrated a radiation source module 250 comprising a number (6 are shown in the exemplary embodiment) of radiation source assemblies 100—in this case, a protective sleeve 102 is shown for each radiation source assembly 100. The specific details for connection of cartridge element 200 to the other elements of radiation source module 250 and the incorporation of radiation source module 250 in a fluid treatment system may be found in U.S. provisional patent application Ser. No. 61/193,686 [Penhale et al.], filed Dec. 16, 2008 and U.S. provisional patent application Ser. No. 61/202,576 [Penhale et al.], filed Mar. 13, 2009.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A radiation source assembly comprising:
   (i) an elongate radiation transparent protective sleeve having a closed distal end;
   (ii) an elongate radiation source disposed in the protective sleeve;
   (iii) a positioning element connected to a proximal portion of the elongate radiation source;
   (iv) a connecting portion secured to a proximal portion of the positioning element, the positioning portion and the proximal portion of the elongate radiation source configured to be in a movable relationship with respect to one another while secured to one another; and
   (v) a support element configured to receive the connecting portion to maintain a distal portion of the elongate radiation source in a cantilevered position with respect to a distal portion of the protective sleeve in a substantially vertical orientation of the radiation source assembly with respect to a direction of fluid flow, the support element having indexing structure relative to the connecting portion so that the elongate radiation source is removable from the elongate radiation transparent protective sleeve while the elongate radiation transparent protective sleeve is in the substantially vertical orientation of the radiation source assembly.

2. The radiation source assembly defined in claim 1, wherein the positioning portion is configured to be in a pivoting relationship while secured to the proximal portion of the elongate radiation source.

3. The radiation source assembly defined in claim 1, wherein the positioning portion is configured to be in a rotatable relationship while secured to the proximal portion of the elongate radiation source.

4. The radiation source assembly defined in claim 1, wherein a distal end of the protective sleeve comprises a sealing element to substantially prevent ingress of fluid to the interior of the protective sleeve.

5. The radiation source assembly defined in claim 1, wherein the protective sleeve is constructed of quartz.

6. The radiation source assembly defined in claim 1, wherein the elongate radiation source comprises at least one centering ring to maintain the elongate radiation source and the elongate protective sleeve in a spaced (e.g., substantially coaxial) relationship with one another.

7. The radiation source assembly defined in claim 1, wherein the positioning element comprises at least one loom portion to secure a plurality of electrical connecters from the elongate radiation source along a portion of the length of the positioning element.

8. The radiation source assembly defined in claim 1, wherein the elongate radiation source comprises a reservoir portion containing a metal amalgam composition.

9. The radiation source assembly defined in claim 8, wherein the reservoir portion is disposed at the distal portion of the elongate radiation source.

10. The radiation source assembly defined in claim 9, wherein the distal portion of the elongate radiation source comprises an amalgam base portion secured thereto, the amalgam base portion receiving at least a portion of the reservoir portion.

11. The radiation source assembly defined in claim 10, wherein the amalgam base portion comprises at least one aperture configured to allow heat dissipation from the reservoir portion.

12. The radiation source assembly defined in claim 11, wherein the amalgam base portion further comprises a flap portion moveable between a first position in which the flap portion at least partially obstructs the aperture and a second position in which the aperture is unobstructed by the flap portion.

13. The radiation source assembly defined in claim 1, wherein the positioning element and the support element are configured to have a single correct engagement position.

14. A radiation source module comprising a support element for securing the module in a fluid treatment system and at least one radiation source assembly defined in claim 1 secured to the support element.

15. The radiation source module defined in claim 14 comprising a plurality of radiation source assemblies secured to the support element.

16. A fluid treatment system comprising a fluid treatment zone for receiving a flow of fluid and at least one radiation source module defined in any one of claim 14, wherein the at least one radiation source module is configured such that the radiation source assembly is disposed in a substantially vertical orientation with respect to a direction of fluid flow in the fluid treatment zone.

17. A radiation source assembly comprising:
   (i) an elongate radiation source disposed in an elongate transparent protective sleeve having a closed distal end;

(ii) a positioning element connected to a proximal portion of the elongate radiation source a connecting portion secured to a proximal portion of the positioning element;

(iii) a connecting portion secured to a proximal portion of the positioning element and configured to engage a support element to maintain a distal portion of the elongate radiation source in a cantilevered position in a substantially vertical orientation of the radiation source assembly with respect to a direction of fluid flow, the support element having indexing structure relative to the connecting portion so that the elongate radiation source is removable from the elongate radiation transparent protective sleeve while the elongate radiation transparent protective sleeve is in the substantially vertical orientation of the radiation source assembly, the positioning portion and the proximal portion of the elongate radiation source configured to be in a movable relationship with respect to one another while secured to one another.

18. The radiation source assembly defined in claim 17, wherein the elongate radiation source comprises at least one centering ring to maintain the elongate radiation source and the elongate protective sleeve in a spaced (e.g., substantially coaxial) relationship with one another.

19. The radiation source assembly defined in claim 17, wherein the positioning element comprises at least one loom portion to secure an electrical connecter from the elongate radiation source along a portion of the length of the positioning element.

20. The radiation source assembly defined in claim 17, wherein the elongate radiation source comprises a reservoir portion containing a metal amalgam composition.

21. The radiation source assembly defined in claim 20, wherein the reservoir portion is disposed at the distal portion of the elongate radiation source.

22. The radiation source assembly defined in claim 21, wherein the distal portion of the elongate radiation source comprises an amalgam base portion secured thereto, the amalgam base portion receiving at least a portion of the reservoir portion.

23. The radiation source assembly defined in claim 22, wherein the amalgam base portion comprises at least one aperture configured to allow heat dissipation from the reservoir portion.

24. The radiation source assembly defined in claim 23, wherein the amalgam base portion further comprises a flap portion moveable between a first position in which the flap portion at least partially obstructs the aperture and a second position in which the aperture is unobstructed by the flap portion.

25. A radiation source assembly comprising:
(i) an elongate radiation source disposed in an elongate transparent protective sleeve;
(ii) a connecting portion configured to engage a support element to maintain a distal portion of the elongate radiation source in a cantilevered position in a substantially vertical and non-parallel orientation of the radiation source assembly with respect to a direction of fluid flow, the support element having indexing structure relative to the connecting portion so that the elongate radiation source is removable from the elongate radiation transparent protective sleeve while the elongate radiation transparent protective sleeve is in the substantially vertical orientation of the radiation source assembly, and
(iii) a positioning portion connected to a distal portion of the connecting portion and a proximal portion of the elongation radiation source, the positioning portion and the proximal portion of the elongate radiation source configured to be in a movable relationship with respect to one another while secured to one another.

* * * * *